US009689817B2

(12) United States Patent
Golan

(10) Patent No.: US 9,689,817 B2
(45) Date of Patent: Jun. 27, 2017

(54) MRI SYSTEM FOR MARGIN ASSESSMENT OF EX-VIVO SAMPLE

(71) Applicant: Clear-Cut Medical Ltd., Rehovot (IL)

(72) Inventor: Erez Golan, Rehovot (IL)

(73) Assignee: Clear-Cut Medical Ltd., Rehovot (IL)

( * ) Notice: Subject to any disclaimer, the term of this patent is extended or adjusted under 35 U.S.C. 154(b) by 425 days.

(21) Appl. No.: 14/386,023

(22) PCT Filed: Mar. 19, 2013

(86) PCT No.: PCT/US2013/032898
§ 371 (c)(1),
(2) Date: Sep. 18, 2014

(87) PCT Pub. No.: WO2013/142459
PCT Pub. Date: Sep. 26, 2013

(65) Prior Publication Data
US 2015/0091564 A1 Apr. 2, 2015

Related U.S. Application Data

(60) Provisional application No. 61/613,587, filed on Mar. 21, 2012.

(51) Int. Cl.
*G01N 24/08* (2006.01)
*G01R 33/30* (2006.01)
(Continued)

(52) U.S. Cl.
CPC ........... *G01N 24/082* (2013.01); *G01R 33/30* (2013.01); *G01R 33/48* (2013.01); *G01R 33/483* (2013.01);
(Continued)

(58) Field of Classification Search
CPC ...... G01N 24/082; G01R 33/30; G01R 33/48; G01R 33/483; G01R 33/56375;
(Continued)

(56) References Cited

U.S. PATENT DOCUMENTS 7,227,630 B1 6/2007 Zavislan
2005/0154291 A1* 7/2005 Zhao ................ G01R 33/56375
600/410

(Continued)

FOREIGN PATENT DOCUMENTS

WO 00/49392 8/2000
WO 2006/088453 8/2006
WO 2011/094659 8/2011

OTHER PUBLICATIONS

PCT Written Opinion and Search PCT/US2013/032898, Nov. 5, 2013.

*Primary Examiner* — G. M. Hyder
(74) *Attorney, Agent, or Firm* — Dekel Patent Ltd.; David Klein

(57) ABSTRACT

A system for margin assessment of an ex-vivo tissue (25) is provided, including a magnetic resonance imaging (MRI) scanner (14) controlled by a control unit (12), and a tissue container (24) for holding a sample of an ex-vivo tissue (25). The MRI scanner (14) includes a coil-magnet assembly (31) including magnets (34), wherein the tissue (25), placed in the container (24), is placed under a constant static magnetic field (Bo), which is induced by the magnets (34), and the container (24) is positioned so the sensitive region is within a measured field of view (FOV) excited by one or more transmit/receive coils (38) operative to generate a time-varying RF B1 electro-magnetic field pointing towards the tissue (25), and wherein the container (24) is fixed on a moving table (40).

15 Claims, 20 Drawing Sheets

(51) Int. Cl.
*G01R 33/48* (2006.01)
*G01R 33/483* (2006.01)
*G01R 33/563* (2006.01)
*G01R 33/341* (2006.01)
*G01R 33/3415* (2006.01)
*G01R 33/381* (2006.01)
*G01R 33/383* (2006.01)

(52) U.S. Cl.
CPC ...... *G01R 33/56375* (2013.01); *G01R 33/341* (2013.01); *G01R 33/3415* (2013.01); *G01R 33/381* (2013.01); *G01R 33/383* (2013.01)

(58) Field of Classification Search
CPC G01R 33/341; G01R 33/3415; G01R 33/381; G01R 33/383
See application file for complete search history.

(56) References Cited

U.S. PATENT DOCUMENTS

| | | | | |
|---|---|---|---|---|
| 2006/0253107 A1* | 11/2006 | Hashimshony | ........ | A61B 34/20 606/1 |
| 2012/0299591 A1* | 11/2012 | Golan | .................... | G01R 33/30 324/309 |
| 2014/0363063 A1* | 12/2014 | Hendriks | ............. | G06T 7/0016 382/128 |

* cited by examiner

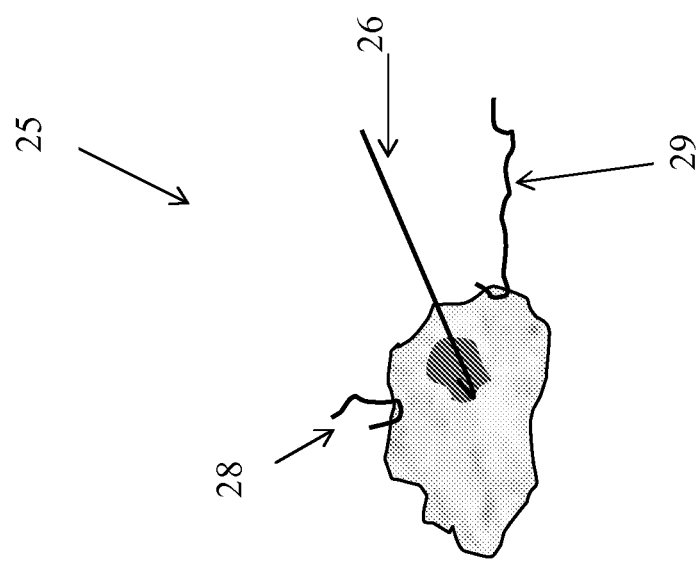
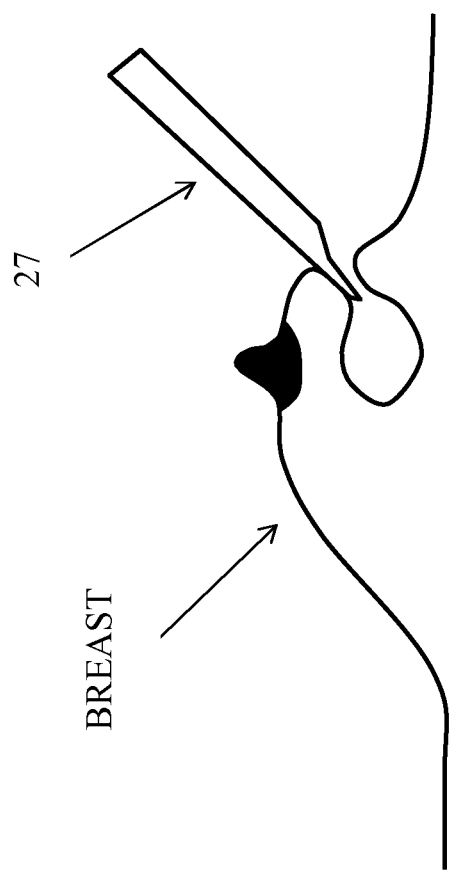
FIG. 2B
FIG. 2A

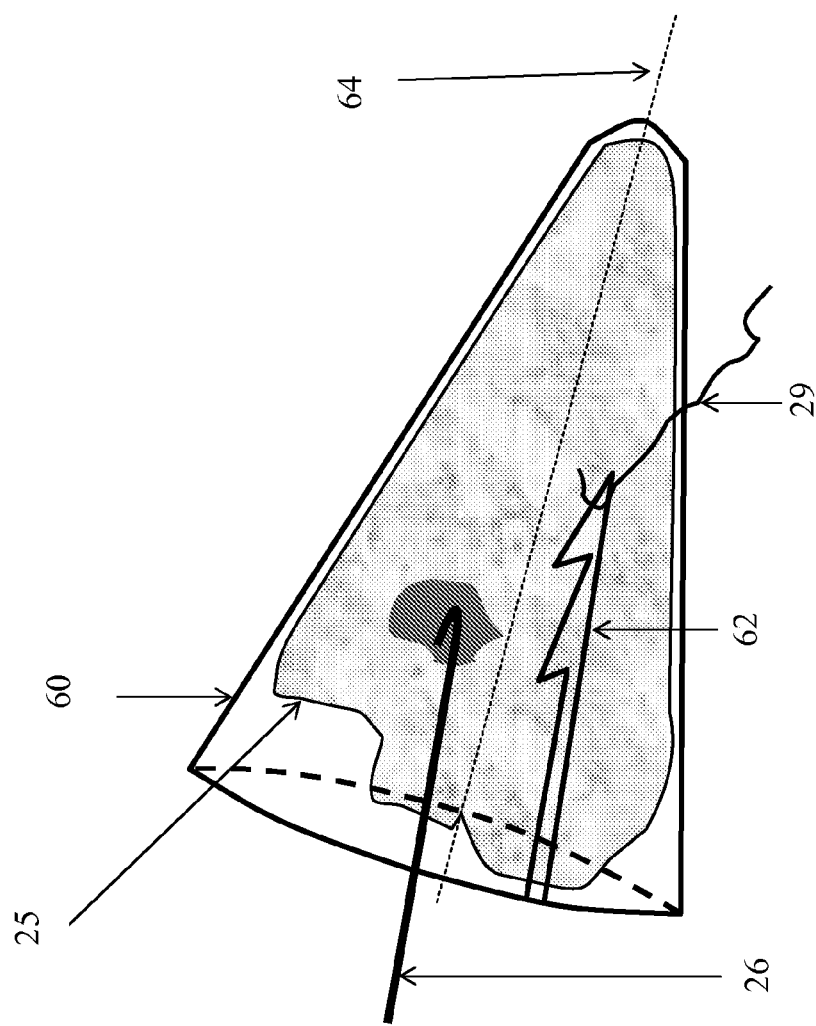
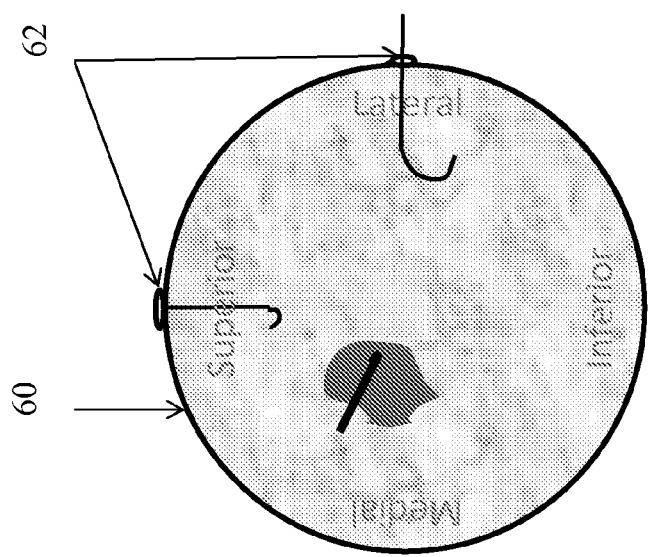
FIG. 18B
FIG. 18A

MRI SYSTEM FOR MARGIN ASSESSMENT OF EX-VIVO SAMPLE

CROSS REFERENCE TO OTHER APPLICATIONS

This application is a U.S. national phase application of PCT patent application PCT/US2013/032898, filed Mar. 21, 2013, which claims priority from U.S. Provisional Patent Application 61/613587, filed Mar. 19, 2012.

FIELD OF THE INVENTION

The present invention relates generally to devices and methods for confirming an existence of a clean margin of healthy tissue around an excised tumor, and for determining the thickness of the margin.

BACKGROUND OF THE INVENTION

When a malignant tumor is found in a breast, generally treatment involves surgical procedure, either mastectomy or lumpectomy, sometimes followed by radiation therapy. The size and location of the tumor are found by different imaging modalities, such as x-ray (mammography), ultrasound, CT, MRI and others. After locating the tumor, a portion of the tissue (lump), including the cancerous portion and a layer of healthy tissue surrounding the cancerous portion, is excised. It is important that the layer of healthy tissue envelop (enclose) the cancerous portion, to ensure that all the malignancy has been removed. This layer is often referred to as a "clean margin".

PCT patent application PCT/US2011/023101 describes a system for margin assessment of an ex-vivo tissue. The system includes an imaging scanner controlled by an imaging control unit, and an ex-vivo sample holder for holding a sample of an excised tissue. The sample holder is sized so that excised lump edges of the excised tissue are forced against a surface of the sample holder such that the edges change shape to have a predetermined geometry. The imaging scanner is positioned relative to the sample holder such that the imaging scanner acquires images (or measurements) not of all the tissue but rather of the edges that have the predetermined geometry and which are in a sensitive region extending into a peripheral margin of the tissue.

SUMMARY OF THE INVENTION

The present invention seeks to provide further devices and methods for confirming an existence of a clean margin of healthy tissue around an excised tumor, as is described more in detail hereinbelow.

BRIEF DESCRIPTION OF THE DRAWINGS

The present invention will be understood and appreciated more fully from the following detailed description, taken in conjunction with the drawings in which:

FIGS. 2A and 2B are simplified illustrations of a lumpectomy procedure, in accordance with a non-limiting embodiment of the present invention.

FIGS. 11-13 are simplified illustrations of an inking margin assembly, constructed and operative in accordance with a non-limiting embodiment of the present invention, wherein FIG. 11 shows the assembly in the coil-magnet assembly, FIG. 12 shows schematically a designated container for inking purposes with its cover on and FIG. 13 shows the container with the cover off;

FIGS. 14 and 15 are simplified illustrations of a photochromic marking pigment (which changes its color upon exposure to electromagnetic radiation) assembly, constructed and operative in accordance with a non-limiting embodiment of the present invention, wherein FIG. 14 shows the assembly in the coil-magnet assembly, and FIG. 15 shows the assembly with the cover off;

FIGS. 17-20 are simplified illustrations of a cone-shaped container, constructed and operative in accordance with a non-limiting embodiment of the present invention, wherein FIG. 17 shows the container open, FIGS. 18A and 18B show the container with a lump pressed therein, and FIGS. 19 and 20 are illustrations of the cone container in the coil-magnet assembly for a lump scan.

DETAILED DESCRIPTION OF EMBODIMENTS

It is noted that the terms "upper", "lower", "above", "below", "left" and "right", and the like, only refer to the sense of the drawings and do not limit the invention in any way.

Figure 1:
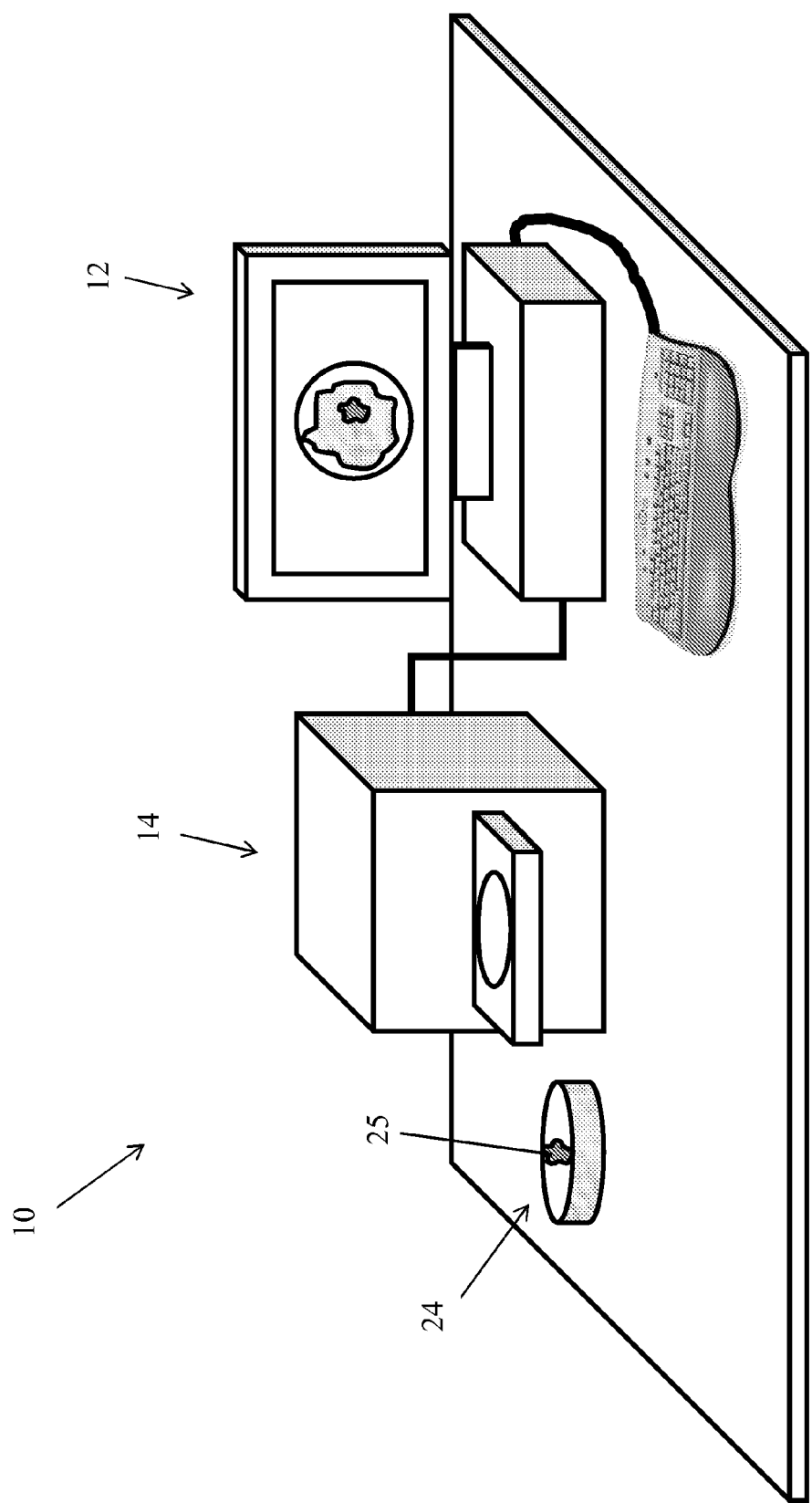
FIG. 1 is a simplified illustration of an MRI system, constructed and operative in accordance with a non-limiting embodiment of the present invention.

Reference is now made to FIG. 1, which illustrates an MRI system 10 for intra-operative margin assessment (positive margin detection of an excised lump or ex-vivo tissue), constructed and operative in accordance with a non-limiting embodiment of the present invention. MRI system 10 enables a physician or technician to receive real-time feedback about the margin's nature.

System 10 includes a control unit 12 (such as a personal computer and the like), which includes software for system management, data analysis and user interface. System 10 further includes an MRI scanner 14, which includes, among other things which will be discussed further below, an RF transmitter-receiver, magnets, transmit/receive coils and a mechanical platform (moving table). An ex-vivo tissue container 24 is provided, which holds the excised lump 25, also referred to as the excised tissue 25 or ex-vivo tissue 25, in a predetermined geometry during scanning thereof by scanner 14. Container 24 is constructed of passive ("safe") MR materials, visually transparent, such as but not limited to, non-conducting, non-metallic, and non-magnetic materials (e.g., a visually transparent plastic).

Reference is now made to FIGS. 2A and 2B, which illustrate a typical lumpectomy procedure. The surgeon or radiologist may insert a tumor marker wire 26 into the breast before the operation under ultrasonic or X-ray guidance to mark the center of the tumor. The surgeon then uses an excision tool 27 to excise tissue around the marked center of the tumor, to receive excised tissue 25. The surgeon makes an effort to excise enough tissue around the tumor so that a clean margin encloses the tumor, while not excising unnecessarily too much normal tissue in order to conserve as much as possible the normal appearance of the breast. The clean margin (i.e., sensitive region) preferably has a thickness of at least a few millimeters (i.e., the thickness around the tumor which is free of cancerous tissue). However, the invention is not limited to this value, and other thicknesses, such as 40 microns to 1 mm or from 1 mm to 10 mm may be considered a clean margin (or other values, depending on the tumor, location and other factors).

Other aspects of the excised lump 25 are also marked. For example, a short thread or other marker 28 may be used to mark the superior aspect, and long thread or other marker 29 for the lateral aspect. Other markers may be employed, such as but not limited to, color-coded pins or ink, pins with different MR signal characteristics, or by any other method.

Figure 3:
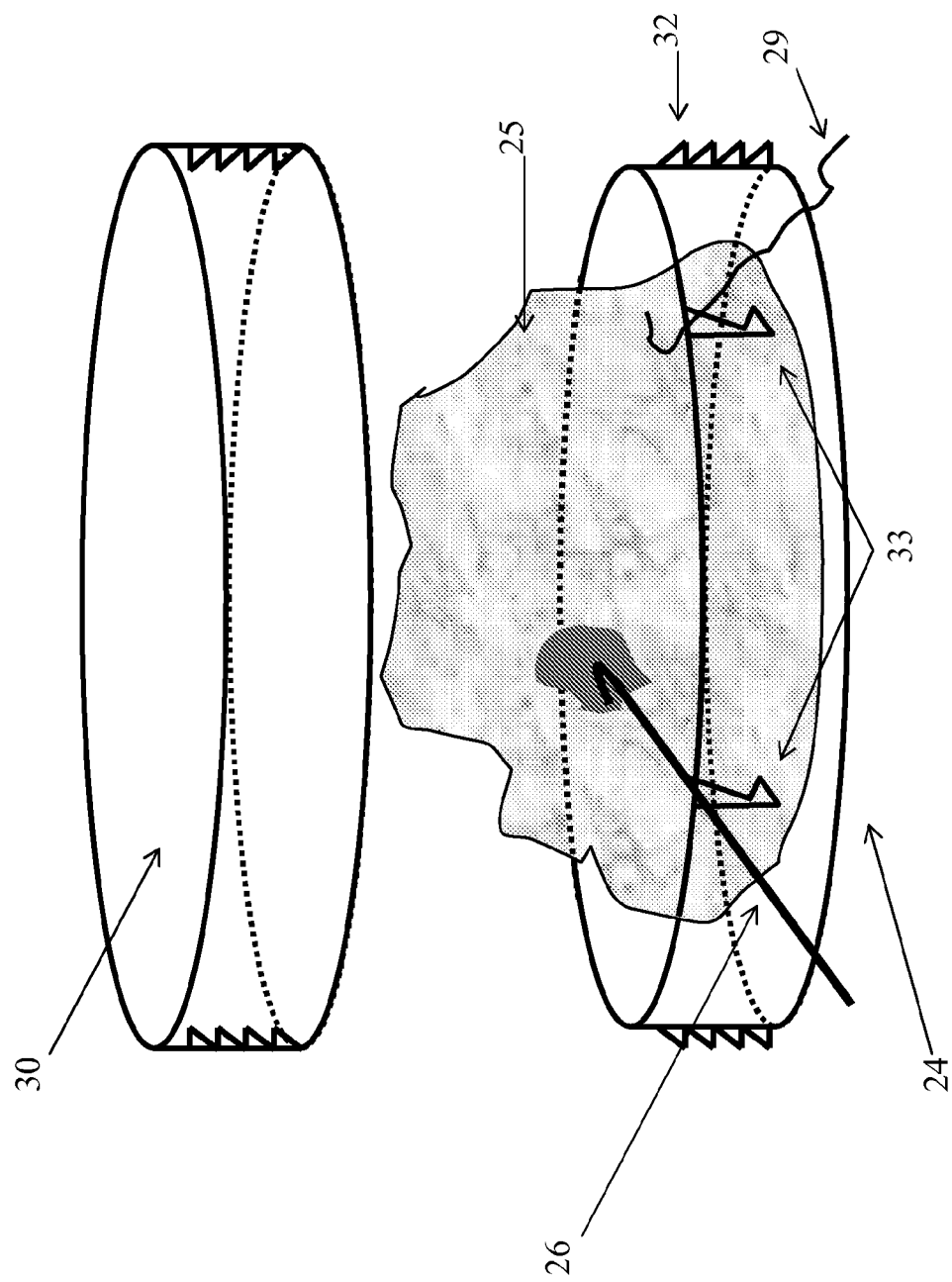
FIG. 3 is a simplified illustration of a flat tissue container, constructed and operative in accordance with a non-limiting embodiment of the present invention.

Reference is now made to FIG. 3, which illustrates a flat tissue container 24, constructed and operative in accordance with a non-limiting embodiment of the present invention. The excised amorphous lump 25 is placed within container 24, which has a well defined geometry, such as a disk-shape, cylinder, etc. A slight pressure may be applied in order to ensure the lump's margins are pressed against the container walls. In this manner, the lump edges generally conform to the inner peripheral shape of container 24. In order to allow tight fitting of the lump edges to the inner surface of container 24, container 24 may be formed with airways to allow trapped air to be released.

Container 24 has a lid 30 which applies a generally constant mechanical pressure on tissue 25. For example, without limitation, lid 30 may be secured to container 24 with linear motion (downward in the sense of the drawings), instead of rotational (screw thread) motion, such as with a ratchet mechanism 32 or similar.

One or more registration elements 33 are provided in container 24, such as orientation slots 33 formed across the walls of container 24. Registration may be accomplished by aligning the wire markers 28 and 29, as well as the tumor marker wire 26, with corresponding orientation slots 33 (and fixing the markers in the slots, such as by threading them through the slots) for positively establishing the desired directional registration. Optionally, additional threads or markers may be used for refined registration purposes.

Figure 4:
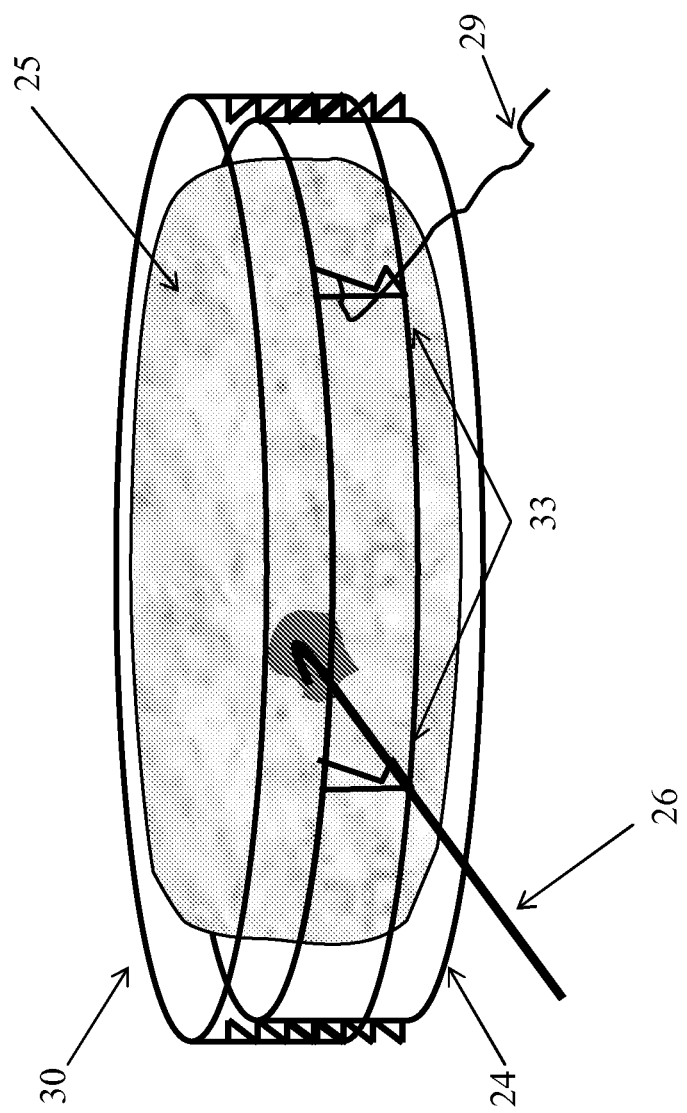
FIG. 4 is a simplified illustration of the flat tissue container of FIG. 3 compressed.
Figure 5:
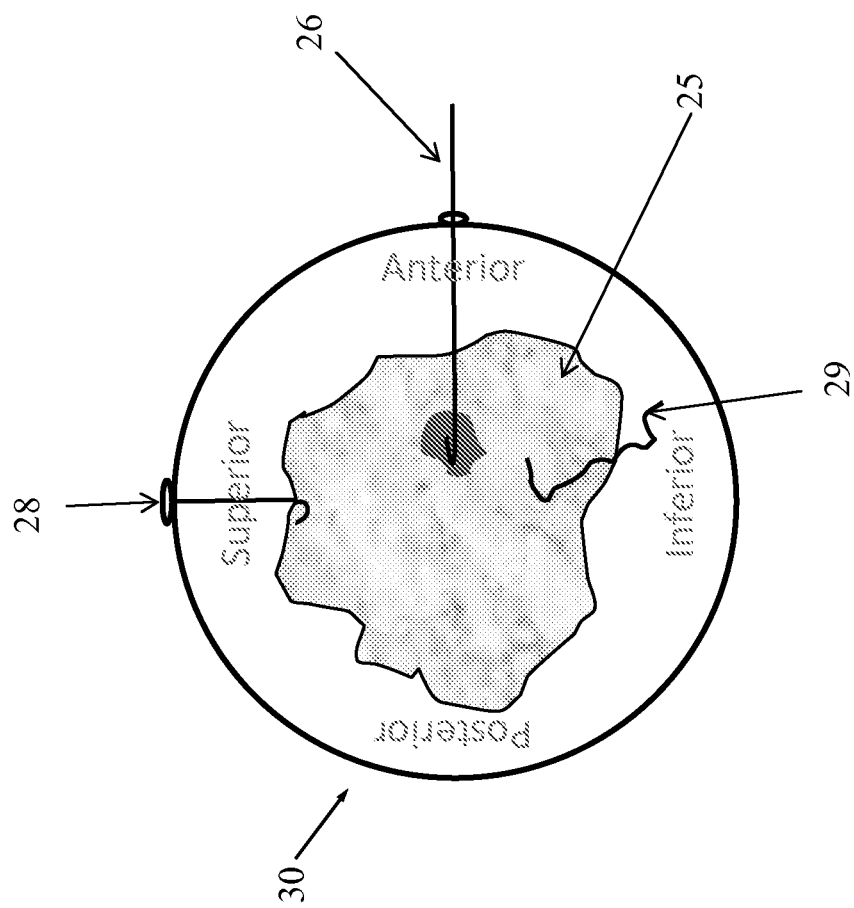
FIG. 5 is a simplified illustration of a lump in the flat container of FIG. 3.

Reference is now made to FIGS. 4 and 5, which illustrate tissue container 24 tightened, prior to the MR scan. The outer margins (in which the clean margins reside) are pressed toward the walls of container 24. As seen in FIG. 5, various notations may be marked on the container lid 30, e.g., indicating the lump's orientation and its actual positioning aspect.

Figure 6:
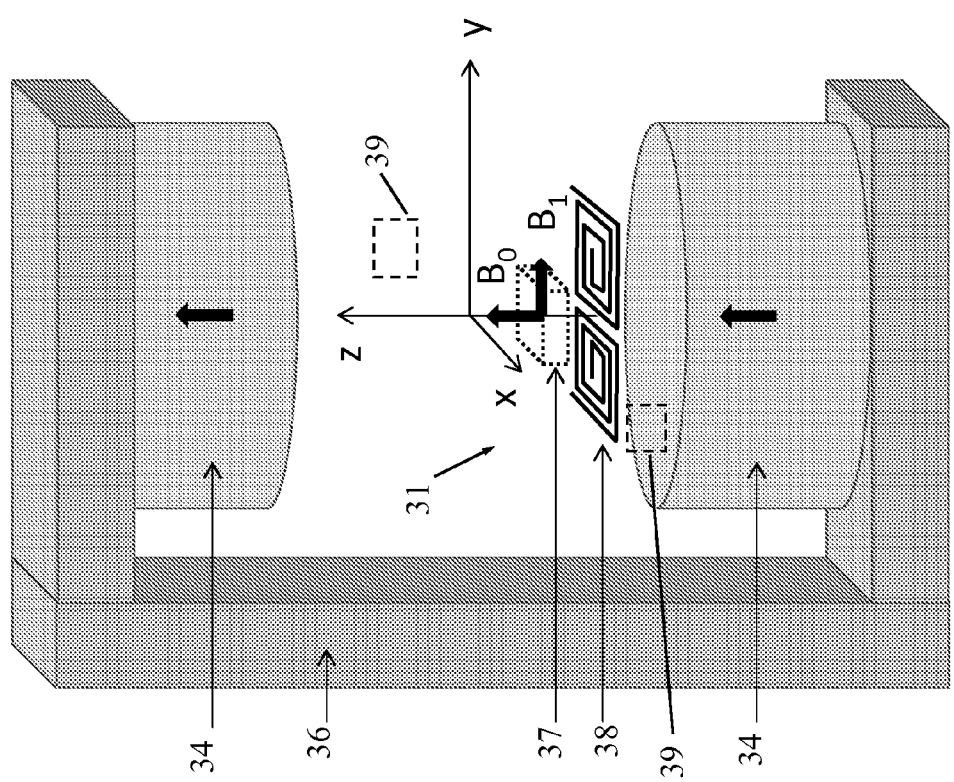
FIG. 6 is a coil-magnet assembly for use with the flat container of FIG. 3 (or cone-shaped container of FIG. 17), constructed and operative in accordance with a non-limiting embodiment of the present invention.

Reference is now made to FIG. 6, which illustrates a coil-magnet assembly 31 for use with the flat container 24. Magnets 34 (permanent or electromagnets) are arranged on a (ferromagnetic, e.g., iron) yoke 36. The excised lump 25, placed in container 24, is placed under a constant static magnetic field ($B_0$), which is induced by magnets 34.

Container 24 (not shown in FIG. 6) is positioned so the outer margins of the tissue are adjacent to the coil's surface during the scan. Tissue lying within the measured field of view (FOV) 37 is excited by a transmit/receive coil 38, generating a time-varying RF $B_1$ electro-magnetic field. Coil 38 is placed between magnets 34 at a position characterized by its $B_0$ and gradient values. The coil lies in a plane, which is oriented parallel, perpendicular or at an angle to the constant magnetic field $B_0$, the orientation being determined by the particular requirements of the procedure. The transmit/receive coil 38 can be designed to be large enough relative to the x/y extent of lump 25, so that the intensity of the $B_1$ field is relatively constant throughout the x/y extent of lump 25. At the same time the transmit/receive coil 38 can be small enough so to effectively excite only nuclear spins that are located only within a relatively narrow (in the x/y dimension) and superficial (in the z dimension) sensitive region and FOV 37 within lump 25, e.g., from the surface up to a few millimeters into the lump 25. The depth of the sensitive region, and therefore FOV 37, into the sample lump is determined by the coil sensitivity profile, and by the homogeneity of the $B_0$ field, which can be relatively good if the sensitive region is up to a few millimeters into the sample. If needed, in order to obtain X/Y resolution, i.e., to separate measurements originating at various x or y positions within the sensitive region, a set of gradient coils 39 can be used, which when activated, produce gradient ($B_G$) fields that are aligned along the +z and −z directions respectively. The gradient coils 39 can create a $B_G$ field pattern that is linear in the x or y directions.

Figure 7:
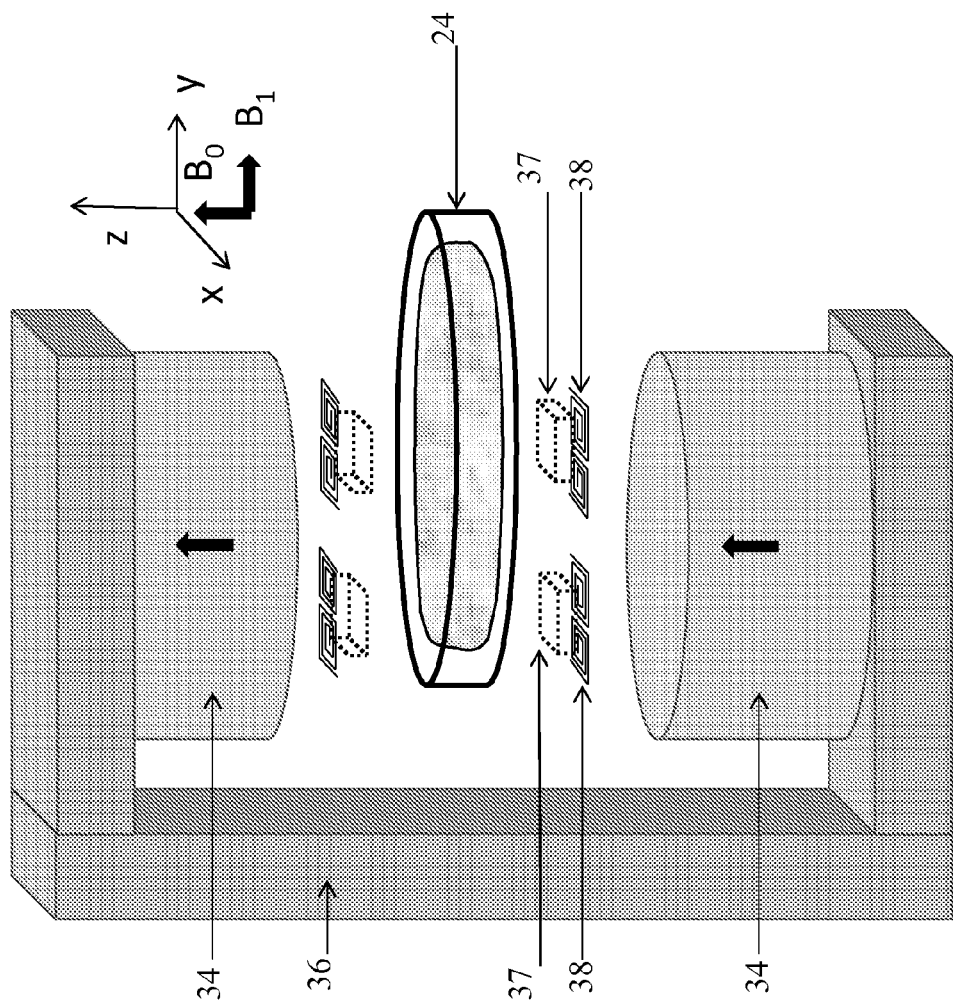
FIG. 7 is a coil-magnet assembly with a multi-coil configuration for use with the flat container of FIG. 3 (or cone-shaped container of FIG. 17), constructed and operative in accordance with a non-limiting embodiment of the present invention.

Reference is now made to FIG. 7, which illustrates a multi-coil configuration, which includes more than one coil 38. The coil array can operate in various modes; the coils can transmit or receive in parallel, in series or any combinations of these modes. Using a multi-coil configuration can shorten the overall scan time of the lump 25 margins.

Figure 8:
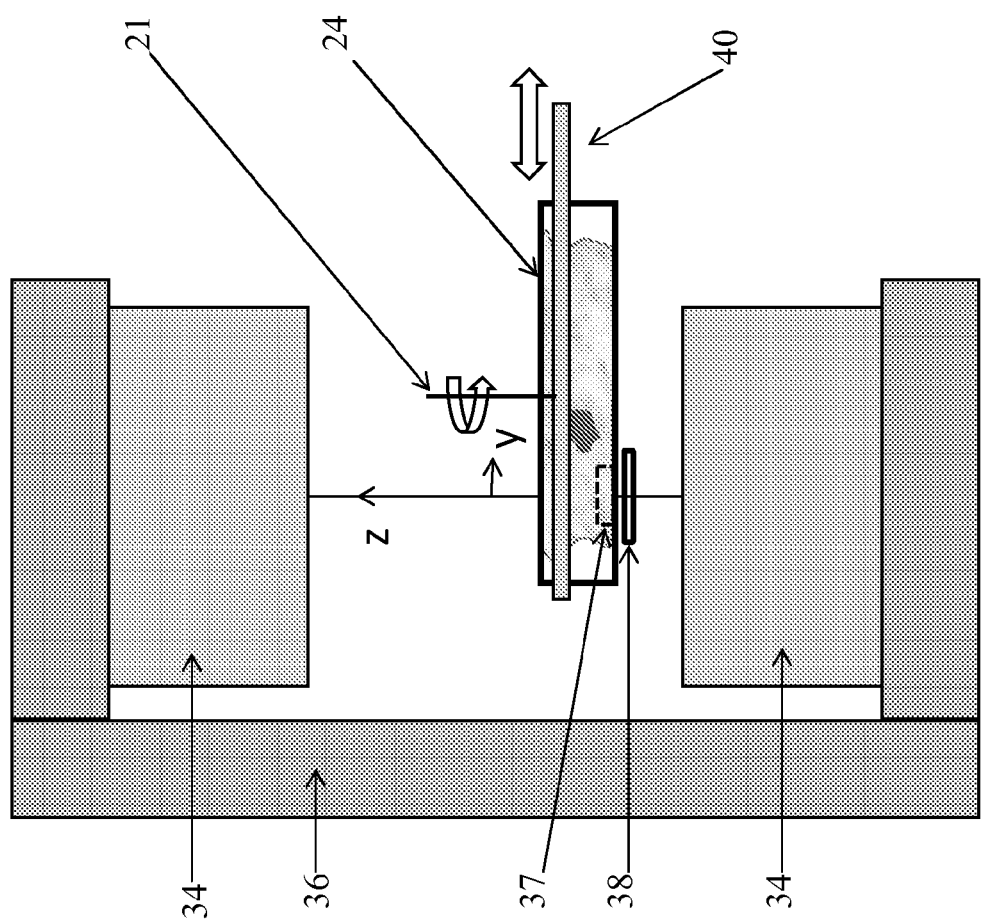
FIGS. 8 and 9 are simplified side-view and top-view illustrations, respectively, of a lump scan, in accordance with a non-limiting embodiment of the present invention.
Figure 9:
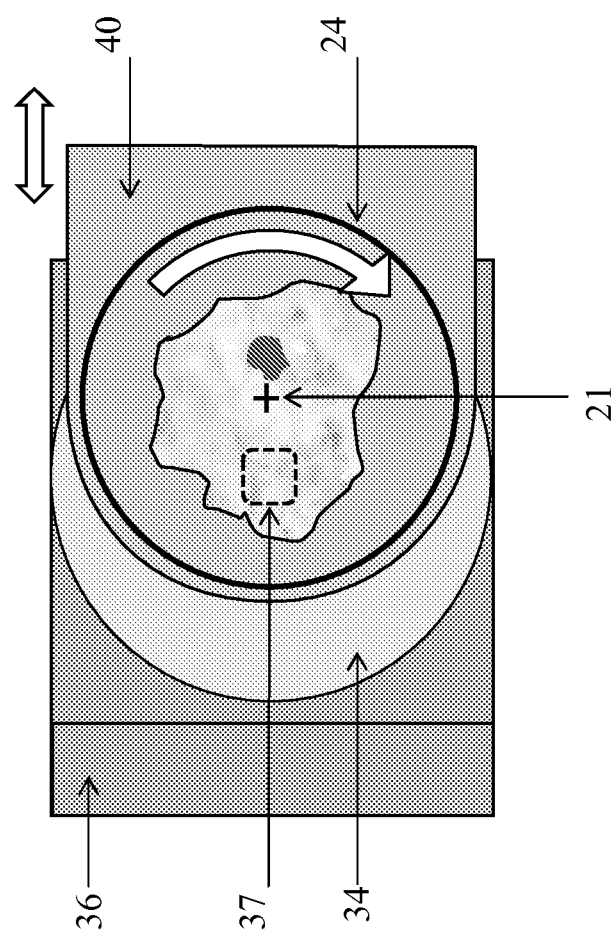
Figure 10:
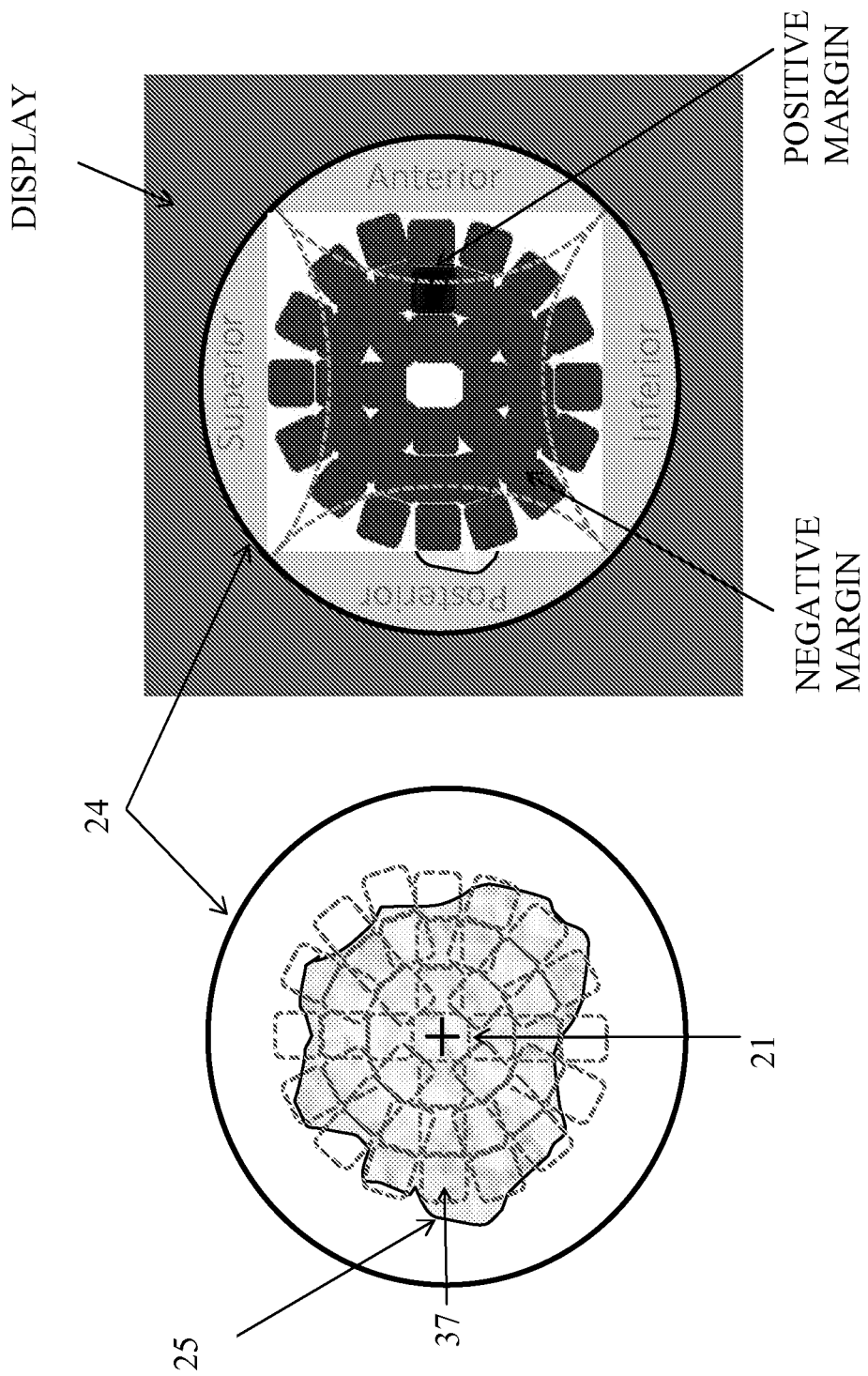
FIG. 10 is a simplified illustration of the lump scan and display.

Reference is now made to FIGS. 8-10, which illustrate a scan of lump 25 in flat container 24. Container 24 is fixed in place on a moving table 40. Table 40 can move linearly in three mutually orthogonal axes and may rotate about one or more of these axes, such as the vertical axis (azimuthal rotation), referred to as rotation axis 21. Table 40 can be moved by a combination of a linear actuator and step motor, for example. Accordingly, the systematic scan can be done in a cylindrical (R,θ), Cartesian (X,Y,Z) or any other coordinate system. During the MR scan, there is relative motion between the moving table 40 and the coil-magnet assembly 31. In the illustrated embodiment, this means moving table 40 moves and coil-magnet assembly 31 remains stationary. However, optionally, coil-magnet assembly 31 could be the item that moves or both coil-magnet assembly 31 and moving table 40 can move.

The lump 25 is rotated in azimuth by table 40. At each angular step, the transmit/receive coil 38 excites and obtains a signal from the sensitive region. Optionally, the x/y-gradient coils 39 can create the x/y-gradient. During azimuthal rotation, an angular (θ) resolution is achieved, wherein signals are received only from a specific angular aperture in the sample lump. When signal acquisition at one angular position is completed, the sample is rotated and a signal from the next angular position is acquired. The field of view 37 is defined by the coil position and the pulse sequence characteristics, such as bandwidth and amplitude; generally the FOV position remains constant.

FIG. 10 illustrates imaging data acquired during the scan, which are presented graphically. The displayed image may include or merge results of various imaging modalities such as X-ray, visual images (from cameras), etc. As illustrated in FIG. 10, a photograph of the lump 25 in the container is displayed, and an overlay of the MRI acquisition data of positive and negative margins is displayed on top of the photograph, such that the coordinates of the MRI data match the coordinates in the photograph.

Figure 11:
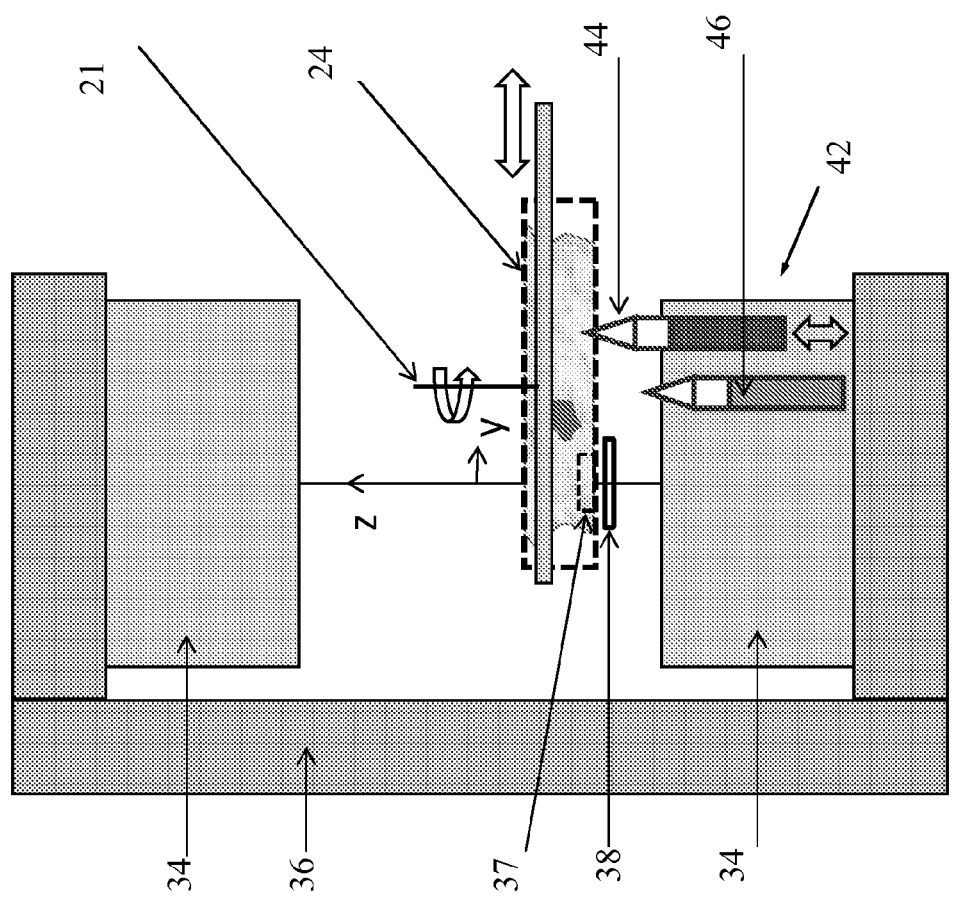
Figure 12:
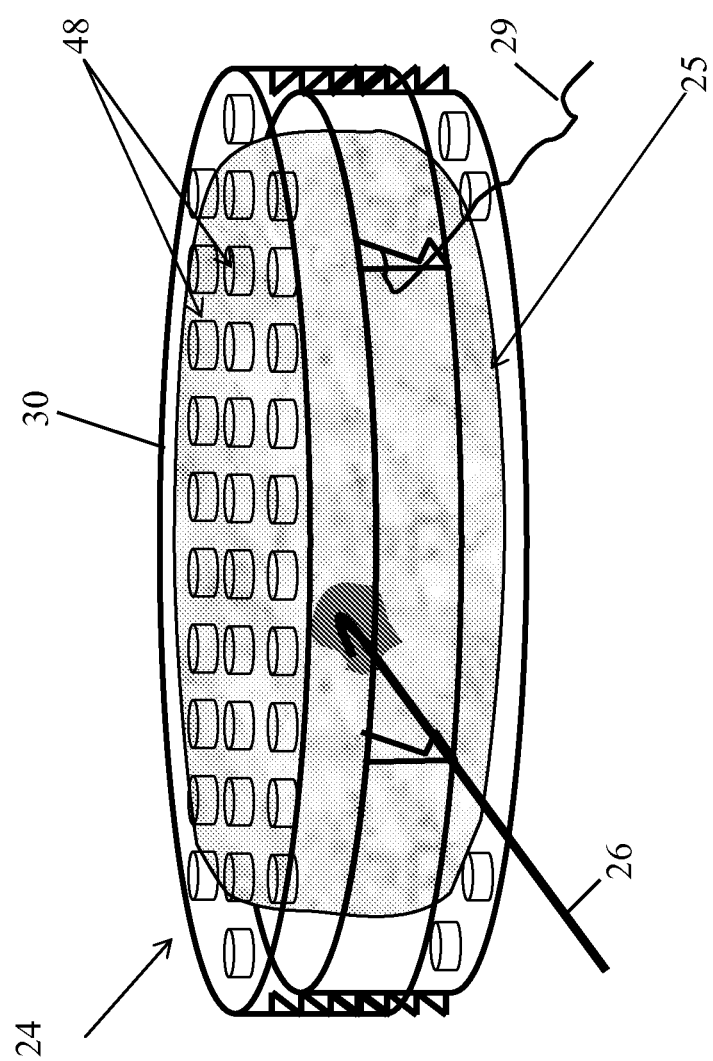
Figure 13:
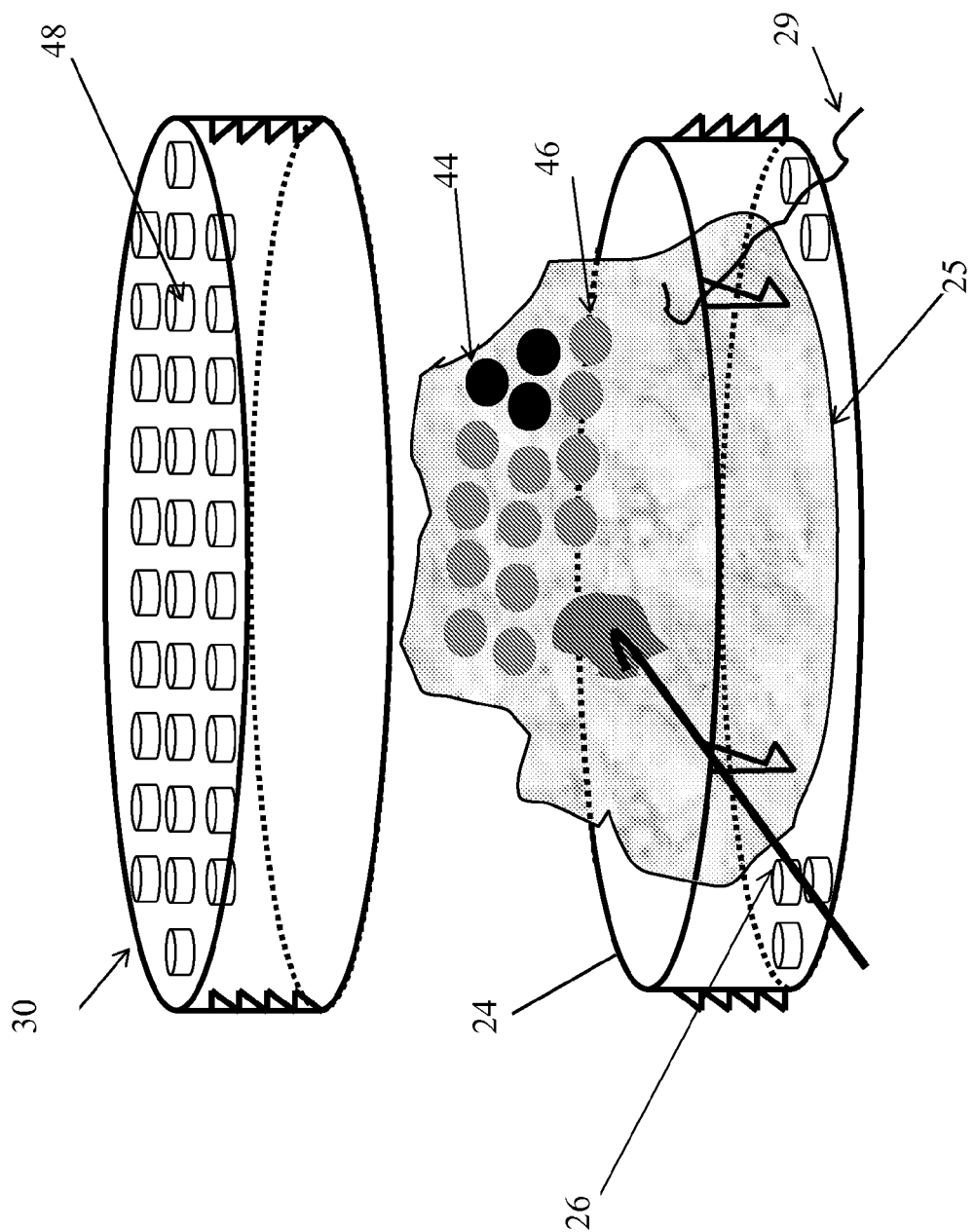

Reference is now made to FIGS. 11-13, which illustrate an inking margin assembly 42, constructed and operative in accordance with a non-limiting embodiment of the present invention. Inking margin assembly 42 includes at least one positive margin ink marker 44 and may also include negative margin ink markers 46. The inking margin assembly 42 may be assembled in or near the lower magnet 34. As seen in FIGS. 12 and 13, lid 30 of container 24 may be formed with inking apertures 48 to enable the ink nozzle to color the tissue.

The ink nozzle will be capable of coloring the sectors found as a "positive margin", which is registered with respect to the registration markers (FIG. 3) of container 24. At the end of the scan, the surgeon can identify those sectors inked as positive margins and consider re-excision and extension of the corresponding in-vivo tissue.

Figure 14:
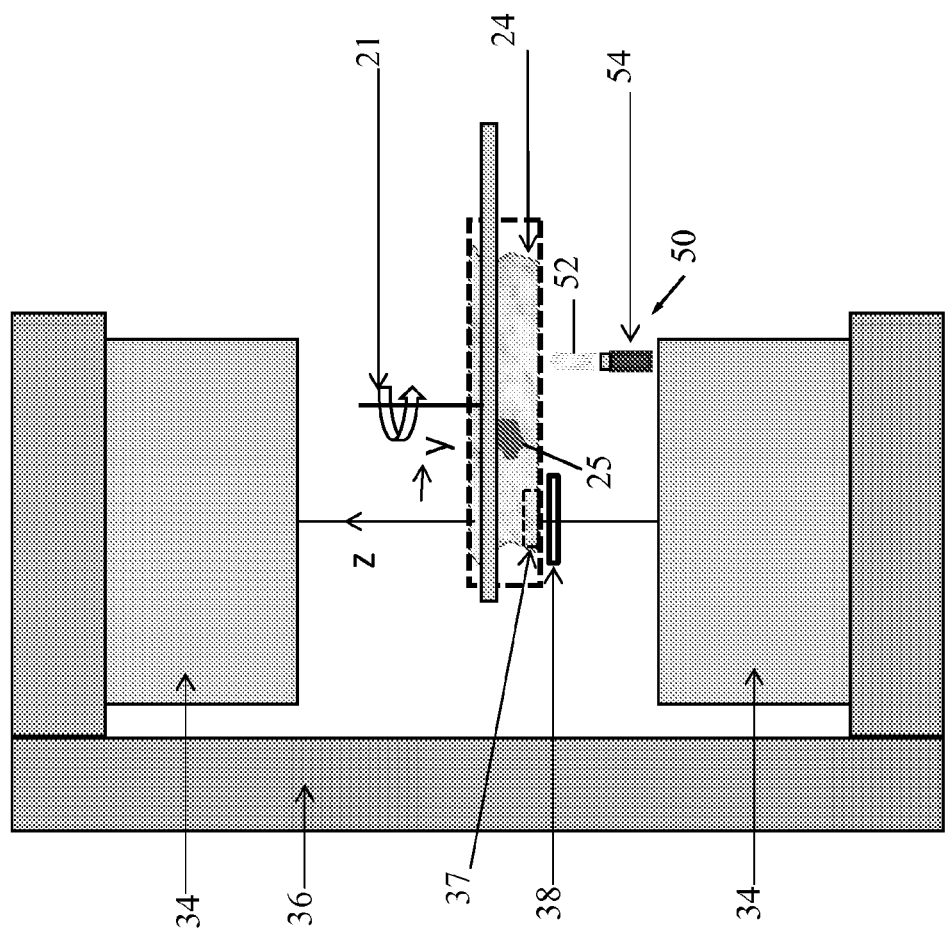
Figure 15:
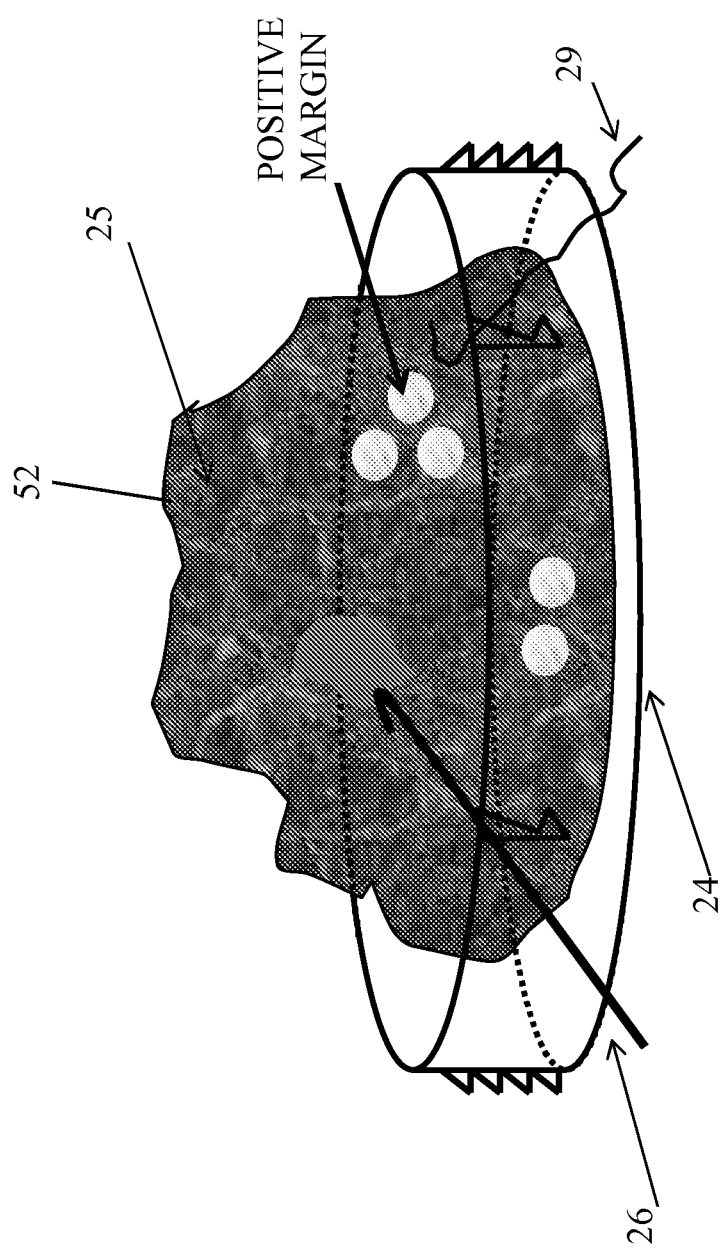

Reference is now made to FIGS. 14 and 15, which illustrate a photochromic marking pigment assembly 50, constructed and operative in accordance with a non-limiting embodiment of the present invention.

Prior to the MR scan, the excised lump 25 is colored with a photochromic pigment 52, available from many manufacturers, which changes its color upon exposure to electromagnetic radiation. Lump 25 may be colored by brushing or spraying the pigment thereon, immersion in the pigment or any other convenient method. The positive margin sectors are locally exposed to an electromagnetic radiation source 54 (e.g., light source 54) which irreversibly (or optionally reversibly after a time delay) changes the visible pigment color. The positive margins are registered with respect to the registration markers (FIG. 3) of container 24. By using the notations on top of the container lid 30, the surgeon can consider re-excision and extension of the corresponding in-vivo tissue.

Figure 16:
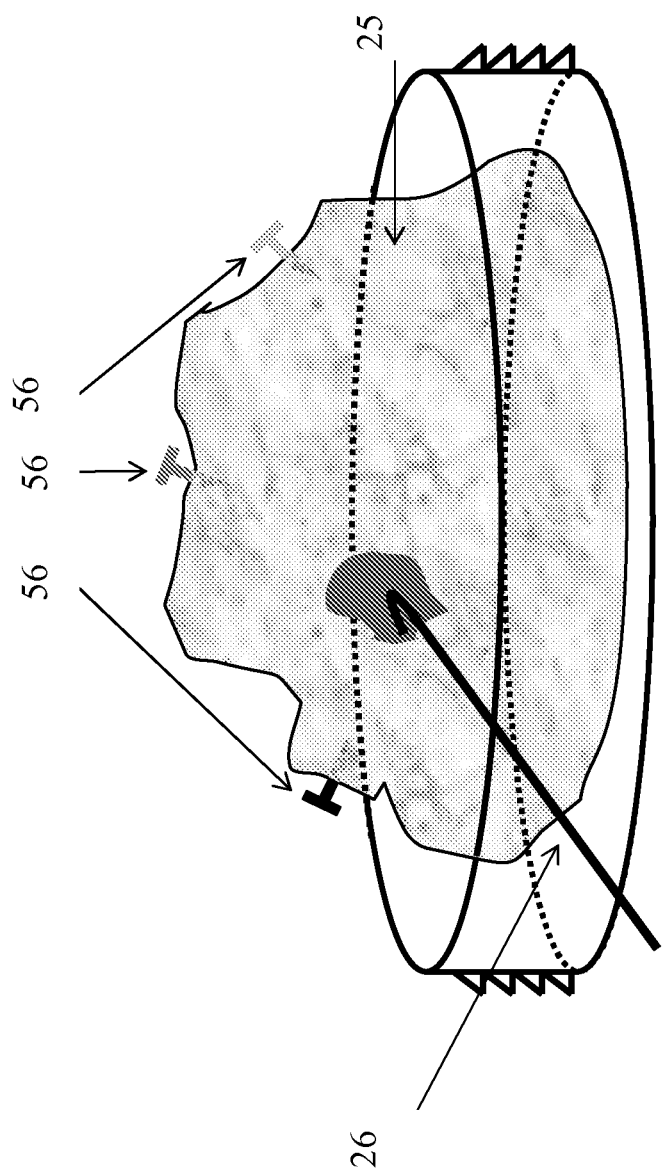
FIG. 16 is a simplified illustration of a set of tacks, which differ by their physical properties, such as color, size or magnetic resonance signal, for example, which can be used for registration purposes with or without respect to the registration markers of the container, in accordance with a non-limiting embodiment of the present invention.
Figure 17:
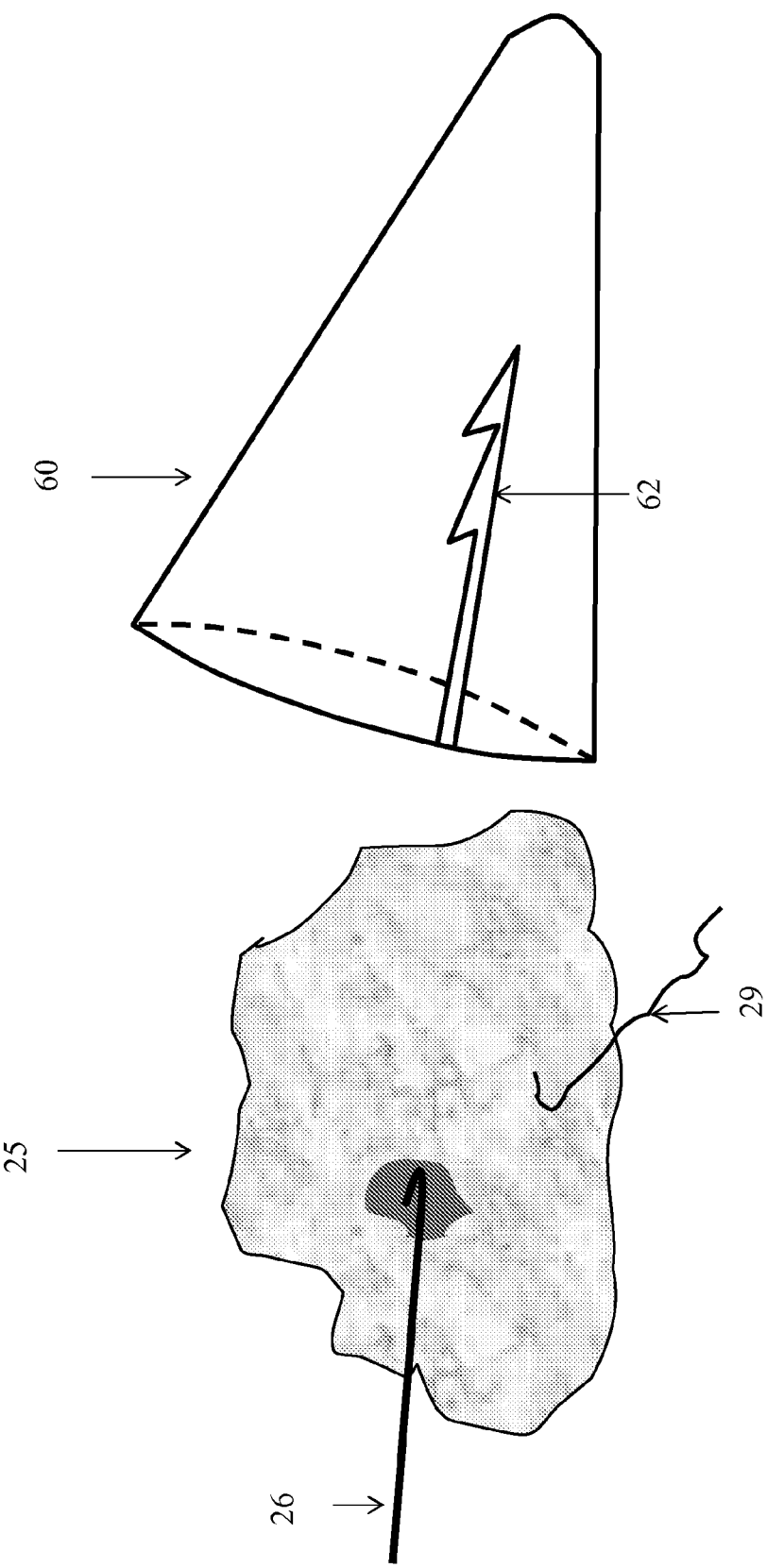

Reference is now made to FIG. 16, which illustrates a set of tacks 56, which can be used for registration with respect to the registration markers (FIG. 3) of container 24. Lump aspects are marked by one or more tacks 56 or similar elements, which are distinct by their physical properties, such as color and geometry. Each tack is assigned and attached to a certain aspect. The tacks can be automatically detected by the system during the scan. In this manner, the system associates a certain scanned FOV to its actual aspect. Alternatively to tacks, different colors of ink can be used by the surgeon, when excising the lump 25, to color its different aspects. The system can then automatically identify these colors as a basis for registering the MRI data with the true lump 25 aspects.

Any combination of several registration methods, such as inking, tacks, etc., can also be used.

Reference is now made to FIGS. 17-20, which illustrate a cone-shaped container 60, constructed and operative in accordance with a non-limiting embodiment of the present invention. Cone-shaped container 60 may be made of various diameters and heights. One advantage of the cone-shaped container 60 is that one size container may fit a relatively wide range of lump sizes, since smaller lumps are pressed further into the cone apex and larger lumps extend further away from the cone apex.

Cone shape container 60 is formed with one or more orientation slots (registration elements) 62, which enable the scan procedure to be performed using cylindrical coordinates, with respect to a central rotation (symmetry) axis 64. The lump 25 is pressed into the cone-shaped container 60, and slight pressure may be applied in order to ensure the lump's margins are pressed against the container walls. In this manner, the lump edges generally conform to the inner peripheral shape of container 60. In order to allow tight fitting of the lump edges to the inner surface of container 60, container 60 may be formed with airways to allow trapped air to be released.

Figure 19:
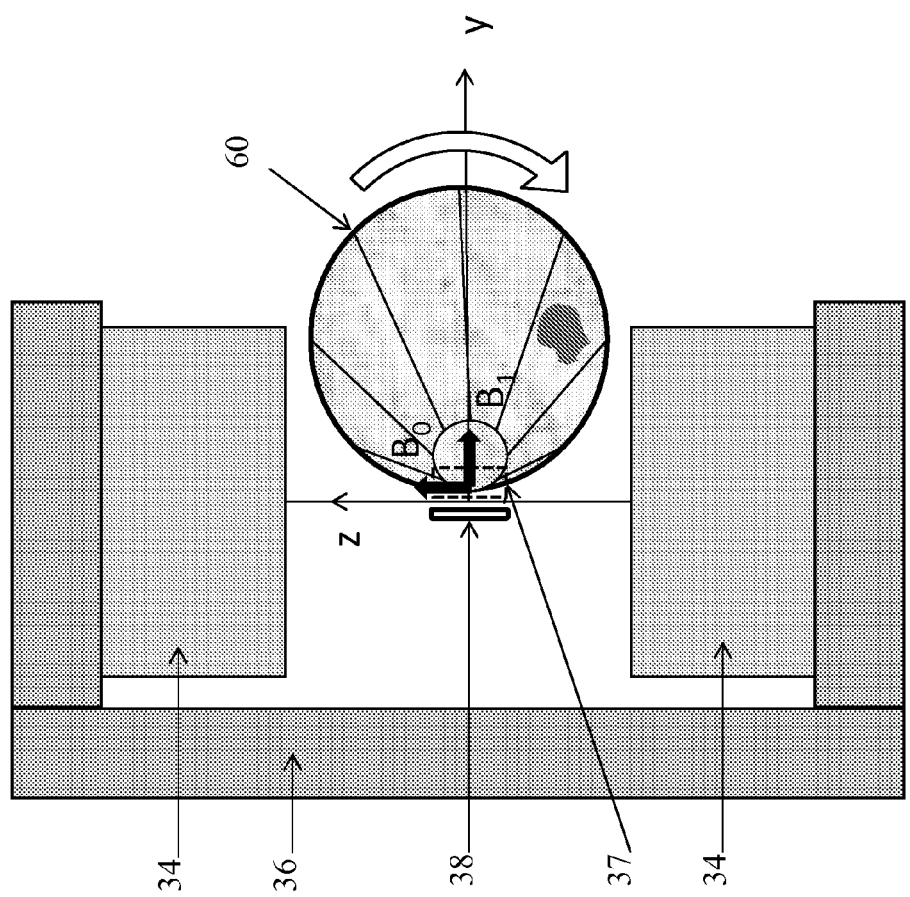
Figure 20:
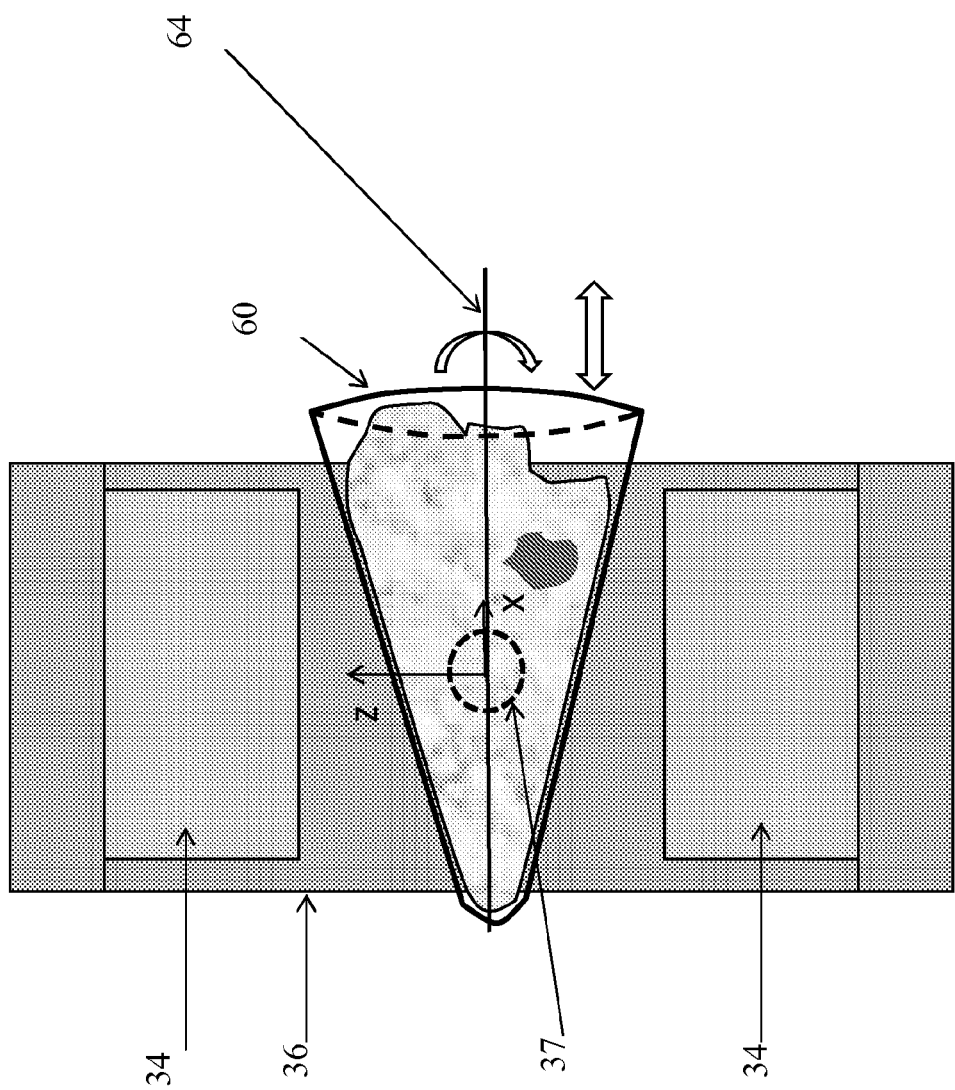

As seen in FIGS. 19 and 20, cone shape container 60 can be used with the apparatus of FIGS. 6-9, except that here container 60 is rotated about rotation axis 64. The cone face is adjacent to the coil 38 throughout rotation about rotation axis 64 (FIGS. 18B and 20), and the scan uses cylindrical coordinates—rotational (θ) and linear\lateral (Z).

What is claimed is:

1. A system for margin assessment of an ex-vivo tissue, comprising:
   a magnetic resonance imaging (MRI) scanner controlled by a control unit; and
   a tissue container for holding a sample of an ex-vivo tissue, said tissue container being sized such that edges of said tissue are forced against an inner surface of said tissue container to have a predetermined geometry, and wherein said MRI scanner is positioned relative to said tissue container such that said MRI scanner acquires images of said edges that have the predetermined geometry and which are in a sensitive region extending into a peripheral margin of said tissue;
   wherein said MRI scanner comprises a coil-magnet assembly comprising magnets, wherein said tissue, placed in said container, is placed under a constant static magnetic field ($B_0$), which is induced by said magnets, and said container is positioned so the sensitive region is within a measured field of view (FOV) excited by one or more transmit/receive coils operative to generate a time-varying RF $B_1$ electro-magnetic field pointing towards said tissue, and wherein said container is fixed on a moving table.

2. The system according to claim 1, wherein said table is movable linearly in three mutually orthogonal axes and rotatable about a rotation axis.

3. The system according to claim 1, further comprising one or more markers in said tissue, wherein said container comprises one or more registration elements for fixing therein said one or more markers.

4. The system according to claim 3, wherein said registration elements comprise orientation slots formed across walls of said container.

5. The system according to claim 4, wherein said lid is secured to said container with linear motion.

6. The system according to claim 4, wherein said lid is secured to said container with a ratchet mechanism.

7. The system according to claim 4, wherein said lid comprises registration notations.

8. The system according to claim 3, wherein said one or more markers comprise one or more tacks.

9. The system according to claim 1, wherein said one or more markers comprise markers of different lengths.

10. The system according to claim 1, wherein said container comprises a lid which applies a generally constant mechanical pressure on said tissue.

11. The system according to claim 1, further comprising an inking margin assembly, comprising at least one positive margin ink marker.

12. The system according to claim 11, wherein a lid of said container is formed with inking apertures providing access for said inking margin assembly.

13. The system according to claim 1, further comprising a photochromic marking pigment assembly, comprising an electromagnetic radiation source operative to change a color of said tissue colored with a photochromic pigment.

14. The system according to claim 1, wherein said container is cone-shaped.

15. A system for margin assessment of an ex-vivo tissue, comprising:
- a magnetic resonance imaging (MRI) scanner controlled by a control unit; and
- a tissue container for holding a sample of an ex-vivo tissue, said tissue container being sized such that edges of said tissue are forced against an inner surface of said tissue container to have a predetermined geometry, and wherein said MRI scanner is positioned relative to said tissue container such that said MRI scanner acquires images of said edges that have the predetermined geometry and which are in a sensitive region extending into a peripheral margin of said tissue;
- and one or more markers in said tissue, wherein said container comprises one or more registration elements for fixing therein said one or more markers.

* * * * *